United States Patent [19]

Alengoz et al.

[11] Patent Number: 4,526,758

[45] Date of Patent: Jul. 2, 1985

[54] STARTING DEVICE FOR SELF-CONTAINED BREATHING APPARATUS

[76] Inventors: Anton S. Alengoz, ulitsa Artema, 108, kv. 27; Anatoly I. Artemenko, ulitsa Levitskogo, 5, kv. 8; Mikhail G. Danilevsky, ulitsa Artema, 163 b, kv. 48; Vladimir K. Kocherga, ulitsa Artema, 163 b, kv. 73; Viktor N. Luchko, ulitsa Slovatskaya, 1, kv. 120; Anatoly E. Margolis, bulvar Shkolny, 4, kv. 128; Vladimir K. Ovcharov, prospekt Kievsky, 5v, kv. 101; Jury A. Shevchenko, ulitsa Lepeshinskogo, 5, kv. 2, all of Donetsk, U.S.S.R.

[21] Appl. No.: 496,065

[22] Filed: May 19, 1983

[30] Foreign Application Priority Data

Jan. 17, 1983 [SU] U.S.S.R. .............................. 3530201

[51] Int. Cl.[3] ........................ A61M 15/00; A62B 7/08

[52] U.S. Cl. .............................. 422/122; 128/202.26; 422/165

[58] Field of Search ............ 102/204, 205, 274, 275.6, 102/429, 487, 488, 530, 531, 275.11; 422/120, 422/122, 126, 165; 128/202.26

[56] References Cited

U.S. PATENT DOCUMENTS

| | | | |
|---|---|---|---|
| 2,667,837 | 2/1954 | Musser et al. | 102/531 |
| 2,741,177 | 4/1956 | Ricards et al. | 102/274 X |
| 3,580,250 | 5/1971 | Oroza | 128/202.26 |
| 3,607,122 | 9/1971 | Hwoschinsky | 128/202.26 X |
| 3,620,683 | 11/1971 | Hwoschinsky et al. | 422/126 |
| 3,786,750 | 1/1974 | Zacharin | 102/274 X |
| 3,933,095 | 1/1976 | Engeli | 102/257 |
| 3,955,931 | 5/1976 | Thompson | 128/202.26 X |
| 3,981,302 | 9/1976 | Veit | 128/202.26 X |
| 4,205,673 | 6/1980 | Wise et al. | 422/165 X |
| 4,246,229 | 1/1981 | McBride et al. | 422/122 |

FOREIGN PATENT DOCUMENTS

| | | | |
|---|---|---|---|
| 3018440 | 11/1981 | Fed. Rep. of Germany | 102/275.6 |
| 0834421 | 5/1960 | United Kingdom | 422/120 |
| 338227 | 5/1972 | U.S.S.R. . | |

*Primary Examiner*—Barry S. Richman
*Assistant Examiner*—B. Patrick Heaney
*Attorney, Agent, or Firm*—Fleit, Jacobson, Cohn & Price

[57] ABSTRACT

A starting device for a breathing apparatus employing chemically-fixed oxygen which incorporates a brick of oxygen generating material superposed by a resilient diaphragm giving support to an ampule with an ignition liquid. The ampule is broken by an ignition means located on the diaphragm under a gas-tight cap in an opening whereof there is provided a resilient bushing containing a removable detent arranged to interact with a retainer of the ignition means so as to keep same in a position ready for operation.

3 Claims, 2 Drawing Figures

STARTING DEVICE FOR SELF-CONTAINED BREATHING APPARATUS

FIELD OF THE INVENTION

The invention relates to constituent components of self-contained breathing apparatus employing chemically-fixed oxygen which are used to protect the respiratory system of man. It may be used to advantage in breathing apparatus of the type worn in collieries during accidents when the atmosphere is unsuitable for breathing, as may be the case due to fire and gas outbursts. Oxygen-breathing apparatus providing short-time protection to the respiratory system of man in hazardous surroundings at chemical plants and in other industries is another field of application of the invention.

BACKGROUND OF THE INVENTION

There is known a starting device for a chemical oxygen generator (cf. Application No. 2,818,250 of Drägwerk AG, Fed. Rep. of Germany; U.K. Patent Specification No. 2,019,729 and U.S. Pat. No. 4,246,229) including a casing with a chemical oxygen generating material therein, an ampule containing an ignition liquid wherein the ampule is cradled adjacent the oxygen generating material, and an ignition means having a spring-loaded thrust bolt held fast in an opening within the casing by a locking pin. A sealing ring at the external end of the thrust bolt tightly fits adjacent the casing, sealing off the interior thereof when the locking pin is withdrawn. The sealing ring thereby prevents oxygen leaks.

The disadvantage of the known design is the possibility of the tilting of the thrust bolt due to fragments of the ampule or an obstacle between the sealing ring and casing (e.g. coarse particles of dust, chip, burrs, etc.) which impairs the sealing effect.

Also known is a starting device for a self-contained breathing apparatus (cf. USSR Inventor's Certificate No. 338,227, Int. Cl. A62B 21/00) incorporating a brick of an oxygen generating material, an ampule containing an ignition liquid cradled in a socket of a resilient diaphgram, and an ignition means in the form of a spring-loaded lever with an ignition pin held ready for operation by a detent.

The disadvantage of this design is its poor reliability resulting from leaks of oxygen through the diaphragm, which can be damaged by the ignition pin in starting the apparatus.

SUMMARY OF THE INVENTION

It is the object of the invention to provide a starting device ensuring reliable functioning of a self-contained breathing apparatus.

The essence of the invention is that the starting device for a self-contained breathing apparatus employing chemically-fixed oxygen incorporates a brick of oxygen generating material with an overlying glass ampule having an ignition liquid for rendering the brick operable on contact therewith. The ampule is cradled in a socket of a resilient diaphragm attached to the brick so that the socket bore faces the brick, above which is located an ignition means for breaking the ampule. The ignition means includes a spring-loaded lever with an ignition pin held ready for operation by a retainer, and is provided with a rigid, gas-tight cap overlying the diaphragm and having an opening stoppered by a blind resilient bushing containing a detent. The detent is arranged to interact with the cap and retainer through the wall of the bushing so as to keep the lever in a position ready for operation and is provided with a means of withdrawing from the bushing.

The starting device designed on the above lines improves the reliability of self-contained breathing apparatus, because any oxygen leakage is prevented even if the diaphragm is damaged in starting the apparatus.

It is expedient that the detent is made of a magnetically hard steel capable of magnetization and the cap is in a diamagnetic material. This plan simplifies the construction of the starting device, for the detent is held fast to the cap by the force of magnetic attraction.

BRIEF DESCRIPTION OF THE DRAWINGS

A preferred embodiment of the invention will be now described by way of an example with reference to the accompanying drawings in which.

DETAILED DESCRIPTION OF THE INVENTION

Figure 1:
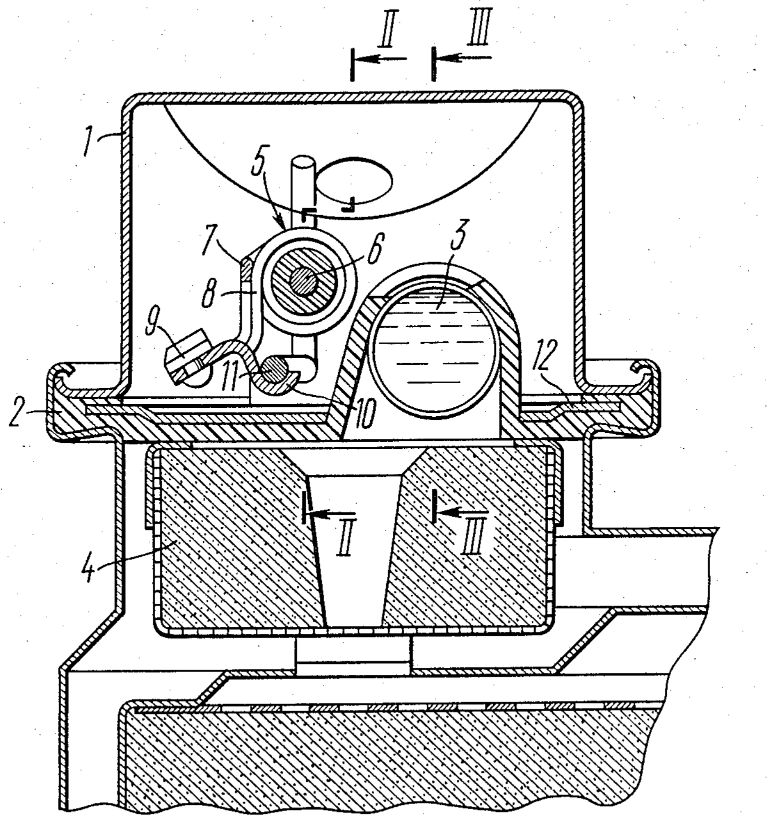
FIG. 1 is a sectional elevation of the starting device of a self-contained breathing apparatus according to the invention and employing chemically-fixed oxygen.
Figure 2:
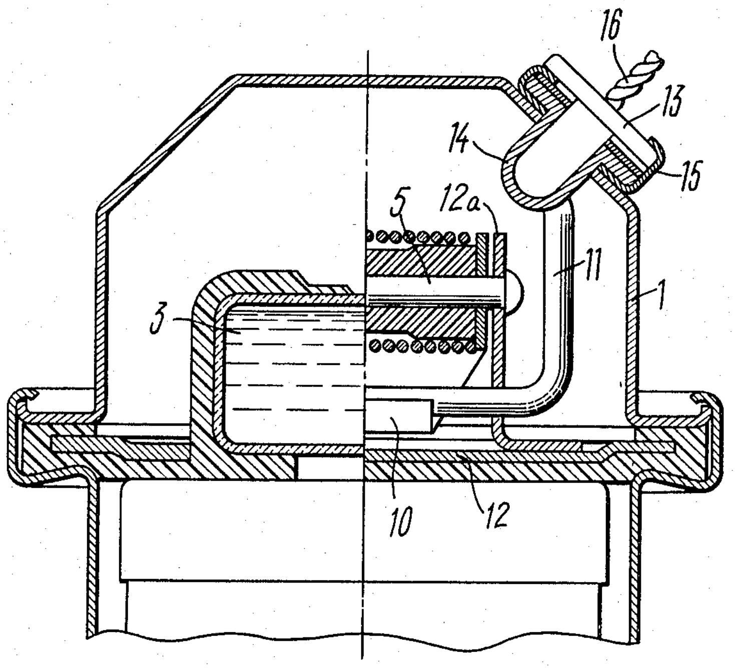
FIG. 2 are sections taken on lines II—II and III—III of FIG. 1.

The starting device for a self-contained breathing apparatus employing chemically-fixed oxygen incorporates a cap 1 (FIG. 1), a resilient diaphragm 2 with an ampule 3 containing an ignition liquid and cradled in a socket of the diaphragm, a brick 4 of oxygen generating material and an ignition means 5. The brick 4, the cap 1, the diaphragm 2 and the ignition means 5 are accommodated in a recess of the regenerative canister (not shown) of the breathing apparatus. The ignition means 5 comprises a lever 7 pivotable about a pin 6 due to the action of a torsional spring 8. An ignition pin 9 with a hook 10 is attached to the end of the lever 7. The hook 10 engages a bend of a retainer 11 which, in its turn, holds the lever 7 in a position ready for operation. The pin 6 and the retainer 11 are fitted to a bracket **12*a* connected to base plate 12, which is held fast to a flange of the regenerative canister together with the cap 1 and the diaphragm 2. The opposite bend of the retainer 11 engages a detent 13 (FIG. 2) fitting into a blind resilient bushing 14 which is accommodated in an opening of the cap 1, thus preventing the retainer 11 from rotating. In an embodiment of the invention, the detent 13 is attached to the cap 1 by bendable tabs 15 and is linked with the removable cover (not shown) of the container, in which the breathing apparatus is contained by a flexible member, e.g., a cord 16. In another embodiment of the invention, the detent is made of a magnetically hard steel capable of magnetization or of an alloy with magnetic properties. If the cap is made of a diamagnetic material (steel), the tabs 15 are redundant, for the detent 13** will be held fast by the force of magnetic attraction.

The disclosed starting device operates as follows. As soon as the cover of the container is removed preparatory to wearing the apparatus, the cord 16 connected to the cover withdraws the detent 13 from the bore of the resilient bushing 14 against the action of the tabs 15 or the force of magnetic attraction. Once the detent 13 is removed, the end of the retainer 11 turns clockwise due to the action of the spring 8 (FIG. 1), setting aside the resilient bushing 14, by an amount causing the hook 10 to disengage the bend of the retainer 11. The lever 7 acted upon by the coiled spring 8 pivots about the pin 6 and strikes the ampule 3 with the ignition pin 9. A crust formed on the surface of the brick 4 is destroyed by the dropping fragments of the ampule 3, facilitating the contact between the ignition liquid and the material of the brick 4. The brick starts to decompose, liberating oxygen in an amount sufficient to meet the user's requirements during the initial period of operation of the breathing apparatus. The moisture and heat formed due to the decomposition of the brick 4, in addition to the liberation of oxygen, promote reactions in the regenerative canister of the breathing apparatus.

The disclosed starting device for a breathing apparatus employing chemically-fixed oxygen according to the invention ensures reliable operation of the apparatus, keeping same always sealed and preventing oxygen leakage. It also eliminates the possibility of inhaling toxic gases by the user.

What is claimed is:

1. A breathing apparatus employing chemically-fixed oxygen, comprising:

a brick of oxygen generating material contained in a canister;

a resilient diaphragm which is positioned above said brick and is provided with a socket having a bore facing said brick;

an ampule containing an ignition liquid serving to liberate oxygen on contact with said brick, said ampule being accommodated in said socket of said resilient diaphragm;

a gas-tight cap located on said diaphragm at the side thereof opposite to the side facing said brick;

an ignition means serving to break said ampule, said ignition means being located on said diaphragm under said cap and including a spring-loaded lever with an ignition pin and a retainer holding said lever in a position ready for operation;

an opening in said cap, said opening located adjacent said lever when said lever is in the position ready for operation;

a blind resilient bushing which is fitted into said opening of said cap to seal off said opening and to extend inside said cap so as to contact said retainer of said ignition means;

a detent which interacts with said cap and is fitted into said resilient bushing so as to interact, through the wall of said bushing, with said retainer of said ignition means, keeping said lever in a position ready for operation;

means for withdrawing said detent from said bushing.

2. A breathing apparatus as claimed in claim 1, wherein said detent is composed of magnetically hard steel capable of magnetization and said cap is composed of diamagnetic material.

3. A breathing apparatus as claimed in claim 1, said apparatus being housed in a container with a removable cover, said cover being connected to said detent by said means for withdrawing said detent wherein said detent withdrawal means is in the form of a flexible member.

* * * * *